United States Patent [19]

Poil

[11] Patent Number: 5,394,132
[45] Date of Patent: Feb. 28, 1995

[54] MAGNETIC MOTION PRODUCING DEVICE

[76] Inventor: James E. Poil, Box 474, Coronach, Saskatchewan, Canada, S0H 0Z0

[21] Appl. No.: 93,669

[22] Filed: Jul. 20, 1993

[51] Int. Cl.$^6$ ............................................. H01F 7/08
[52] U.S. Cl. ................................. 335/232; 335/222; 335/223; 335/259; 335/264; 335/267
[58] Field of Search ................... 335/222–224, 335/229–234, 242, 257, 259, 264, 267; 623/24

[56] References Cited

U.S. PATENT DOCUMENTS

| | | | |
|---|---|---|---|
| 3,750,067 | 7/1973 | Fletcher et al. | 335/296 |
| 4,176,411 | 12/1979 | Runge | 3/1.7 |
| 4,516,102 | 5/1985 | Rask | 335/267 |

*Primary Examiner*—Gerald P. Tolin
*Assistant Examiner*—Raymond M. Barrera

[57] ABSTRACT

A motion producing device in the form of a linear actuator, circular pump, or a robotic or prosthetic limb which functions to produce many kinds of work is provided. The device includes a linear series of alternately spaced fixed and polarity reversible magnets. The fixed and polarity reversible magnets may have more than one magnet assembled as a force unit of magnets of fixed polarity or reversible polarity which is surrounded by a rigid electrically insulating material and that carries rigid electrical conductors in the form of tubes. Between each magnetic force unit is an elastic electrically insulating material allowing expanding or shrinking of the distance between the magnetic force units in accordance with the polarity reversal of the reversible magnetic force units. The elastic expansion or contraction material carries flexible elastic tubes that connect with the rigid tubes to hold a current carrying electrolyte to carry electrical current from a D.C. battery to the magnets when they are electromagnets. Various types of guides are used to prevent lateral movement of the magnets. A second embodiment also has magnetic force units of the fixed and reversible polarity type but has slideable electrical contacts in an external side guide and requires no electrolyte or tubes. A further modification utilizes the original rigid tubes and provides guide rods as slideable electrical contacts to slideably engage the rigid tubes which are metal. Again the disposing of the elastic flexible nonconductive tubes in the elastic nonconductive filler material between adjacent magnets is possible.

16 Claims, 6 Drawing Sheets

MAGNETIC MOTION PRODUCING DEVICE

This application relates to a motion producing device utilizing magnetic lines of force and in particular to a robotic or prosthetic device of unlimited application.

BACKGROUND OF THE INVENTION

Magnets have been in use for hundreds of years probably the first being for magnetic compasses for navigation. The industrial revolution saw new uses develop such as solenoids, metal lifting cranes and pumps for moving liquid metals in nuclear reactors. All magnets have what is called North and South poles with lines of force eminating therefrom in a magnetic circuit. With any two magnets like poles repel and unlike poles attract. This is the basis for movement produced in the instant invention. The distances between the magnets are important since the force varies inversely as the square of the separating distance. Basically used is the electromagnet since the strength of it can be easily controlled since the strength depends on the amperage in the circuit times the number of turns of wire about a Ferromagnetic core.

Attempts have been made in the past to utilize magnetic force for movement of robotic and prosthetic devices, the one most closely related to applicants device is U.S. Pat. No. 5,062,855 to Rincoe Nov. 5, 1991. This patent teaches a plurality of magnets including at least one electromagnet linearly aligned so that the law of magnets can be applied to cause an expansion or contraction. It is the reversal of the polarity of selected electromagnets that causes the expansion or contraction. So far this patent appears basically the same as applicants invention. However, "855" diverges in that the preferred embodiments require that the opposite end of the magnets be hinged, that the magnets are covered by an outer sheath or skin carrying electrical conductors with contacts and that sensors are used in the hinge discs and on the outer surface of the skin or glove. Applicants device differs in that it includes rigid electrically insulating material surrounding the magnets, elastic electrically insulating material mounted between each adjacent fixed and reversible polarity magnets, guide means, electrolyte carrying tubes both metal and flexible types or a slideable guide electrical carrying means and a cable digit control.

SUMMARY OF THE INVENTION

The present invention provides an electrically controlled motion producing device for pumping, for prosthetic devices or for general application. A first embodiment of the device is formed of a series of magnetic force units which are alternately, fixed polarity and reversible polarity magnets surrounded by a rigid electrically nonconductive material having rigid electricity carrying means embedded therein. Separating the adjacent magnetic force units is an elastic electrically nonconductive material having elastic electricity carrying means connected to the rigid electricity carrying means. The connected electricity carrying means carries an electrolyte which is conductively energized by an electrical source providing electrical power to the magnetic force units. A polarity reverser is provided to reverse the polarity of the reversible magnets when motion is required. A protective sheath or other guide means generally covers the device.

A second embodiment of the device has a magnetic force unit whose magnets are connected to sliding contacts protruding from the side of the unit and whose guide means carries a conductive strip to carry power from the power source to the magnets.

Using either the first, second or a variation or combination of these embodiments, various prosthetic devices can be produced such as a moveable forearm, wrist and fingers.

From the above summary it is readily discernible that a principle object of the above invention is the provision of a simple basic movement device utilizing the laws of magnetic repulsion and attraction.

A further object of the invention is the provision of a movement device that can basically be produced from a series of like magnetic force units.

Another object of this invention is the provision of a movement device that can be of various lengths and forms such as rectilinear or curvilinear.

Yet another object of this invention is the provision of a movement device that is readily adapted for use in many aspects of the mechanical field as well as the medical field where it is capable of simulating muscular movement for remotely or directly controlled robotics or prosthetics.

These and other objects of the present invention will become readily apparent as the following description is read in conjunction with the accompanying drawings wherein like reference numerals indicate like elements throughout the several views.

DETAILED DESCRIPTION OF THE DRAWINGS

Figure 1:
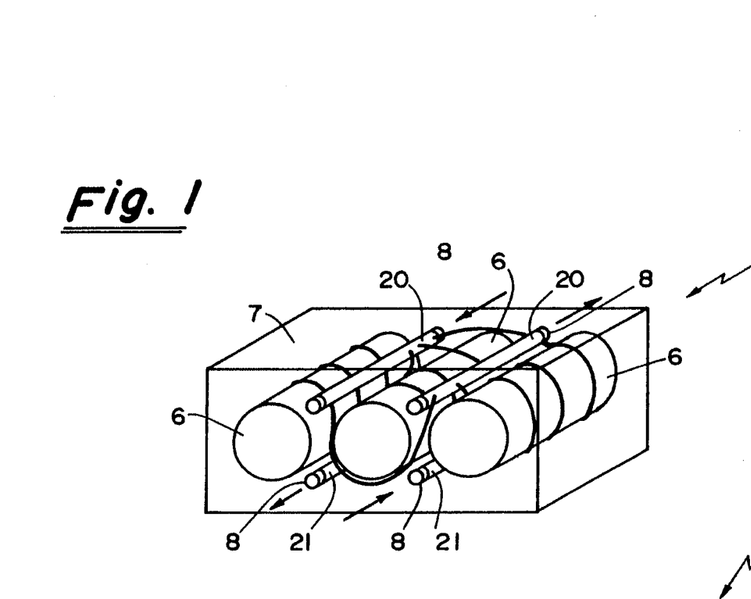
FIG. 1 is a perspective view of a first embodiment of the basic magnetic force unit.

Referring to FIG. 1 there is shown in perspective a first embodiment of a basic magnetic force unit 1. This unit 1 can be used either as a fixed polarity unit or as a reversible polarity unit and when a series of these units are alternately placed as fixed and reversible it forms a basic motion producing device 10 of FIG. 2. The magnetic force unit 1 includes 1 or more electromagnets 6 placed side by side and surrounded by a rigid electrically insulating or electrically nonconductive material 7. Also surrounded in the electrically nonconductive material 7 are four rigid electrolyte or electricity carrying tubes 20, 20 and 21, 21. The tubes 21 21 are generally metallic and form part of a first electrical circuit. The tubes 20 20 are also generally metallic and form part of a second electrical circuit, all the tubes 20 20, 21 21 can be identical for simplicity. Each of the tubes 20 20, 21 21 have at their ends, couplers 8. The three electromagnets shown are connected to the second circuit in parallel at tubes 20 20 and feed fixed polarity units 1a.

Figure 2:
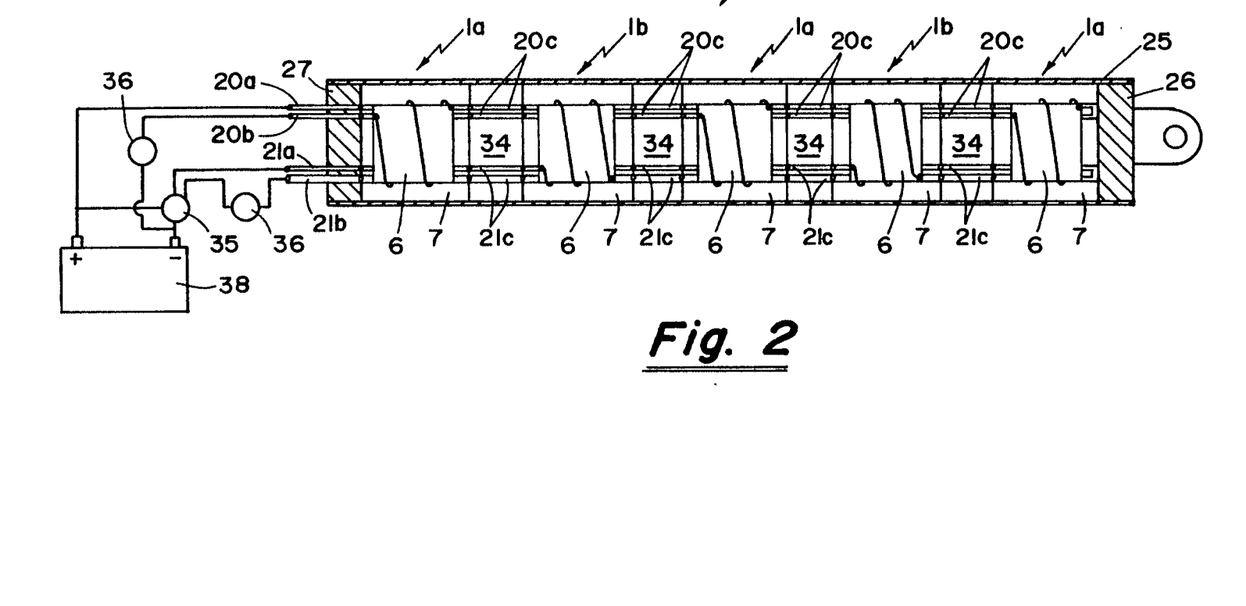
FIG. 2 is a sectioned side elevation of a powered motion producing device using a series of the basic magnetic force units.

Referring now to FIG. 2 there is sectioned a basic motion producing device 10 powered by a D.C. battery 38. The basic motion producing device 10 is made up of a series of magnetic force units 1. The fixed polarity magnetic force unit has been designated 1a and the reversible polarity magnetic force unit has been designated 1b. The units 1a and 1b are so designated for identification only but can in fact all be structurally identical to the basic magnetic force unit 1. The basic force unit 1 can be changed from 1a to 1b by turning the unit upside down so that tubes 20 20 now become tubes 21 21 in the reversible polarity circuit.

The electromagnets 6 in units 1a are connected in parallel to the second circuit with leads 20a 20b which operates on a fixed polarity but is controlled by a rheostat 36. The electromagnets 6 in units 1b are connected in parallel to the first circuit with leads 21a 21b which operates on a reversible polarity and is controlled by a rheostat 36 and a polarity reverser 35.

Between each adjacent magnetic force unit is an elastic nonconductive filler material 34. Embedded in elastic material 34 are flexible electrolyte carrying tubes 21c for the first circuit and tubes 20c for the second circuit. The flexible tubes 20c in each filler material 34 are coupled by couplers 8 to rigid tubes 20 in each of the magnetic force units 1a or 1b and the flexible tubes 21c are coupled by couplers 8 to rigid tubes 21 in each of the magnetic force units 1a or 1b.

At the powered end of the motion producing device 10 is an electrical connection end cap 27 which carries the power leads 20a 20b 21a 21b. The end cap 27 may also include conductive plugs to join the power leads 20a 20b 21a 21b to the first electromagnetic unit 1a. The end cap 27 commonly engages a retainer to have a fixed or reaction end for the motion producing device 10.

At the moveable end of the motion producing device 10 is a coupler end cap 26 with a clevis to be connected to a link or other motion transfer means. Covering the motion producing device 10 is normally an elastic sheath 25 which serves as a protection cover and guide.

It is to be realized that while electromagnets 6 have been used for the fixed polarity units permanent magnets may be substituted thereby obviating all need for the second circuit. Electromagnets 6 are however more desirable in that their strength may be readily and easily adjusted by a rheostat 36 for a more versatile device.

In operation, a power supplied to the first and second circuits through leads 21a 21b and 20a 20b respectively will cause an attraction or repulsion of the alternate magnetic force units 1a 1b causing the coupler end cap 26 to move away or towards a fixed electrical connection end cap 27. The strength of the magnetic force being controlled by rheostats 36 and the direction of motion being controlled by the polarity reverser 35 in the first circuit.

Figure 3:
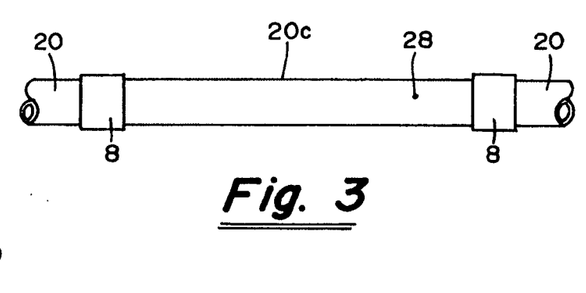
FIG. 3 is a side view of the rigid electrolyte carrying tubes of a magnetic force unit joined by a flexible electrolyte carrying tube.

In the FIG. 3 illustration there is shown a flexible elastic tube 20c which is normally found in the elastic nonconductive filler material 34 joined by couplers 8 to rigid tubes 20 which are normally metal. Several of these tubes 20 and 20c when joined are included in a second circuit and carry an electrical carrier in the form of an electrolyte 28. Rigid tubes 21 and elastic tubes 21c similarly are included in a first circuit also carrying an electrolyte for current transmission.

Figure 4:
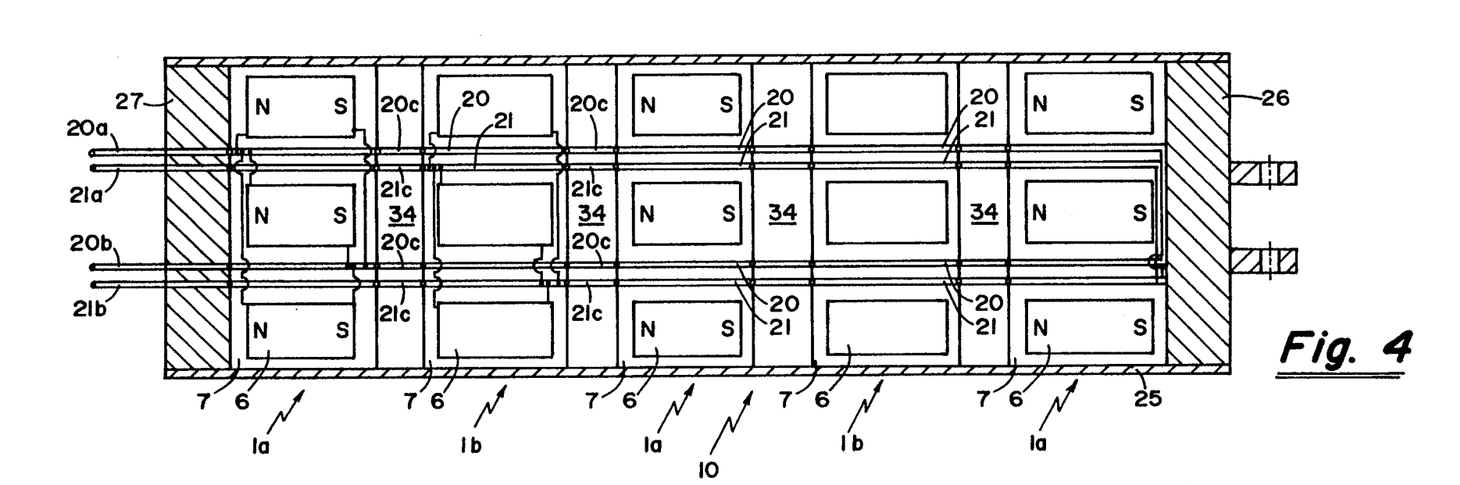
FIG. 4 is a sectioned plan view of a series of magnetic force units assembled as a motion producing device.

Referring now to FIG. 4 there is shown a sectioned plan view of the motion producing device of FIG. 2. The basic magnetic units are again shown as 1a for the fixed polarity units and 1b for the reverse polarity units. It is more clearly shown how each of the magnetic force unit electromagnets 6 are connected in parallel to their respective circuits with the electrically nonconducting elastic filler material 34 filling the space between the units. The second circuit is again shown with the leads 20a 20b connected firstly to the rigid tubes 20 20 embedded in a rigid nonconductive material 7 in a fixed polarity magnetic force unit 1a then continuing via flexible elastic tubes 20c in the elastic filler material 34 and on through the remaining magnetic force units 1b 1a 1b 1a and separating filler materials 34 but being connected electrically only to the three 1a magnetic force units. The first circuit is again shown with the leads 21a 21b connected to rigid tubes 21 21 embedded in a rigid nonconductive material 7 in a reversible polarity magnetic force unit 1b then continuing via flexible elastic tubes 21c in the elastic filler material 34 and on through the remaining magnetic force units 1a 1b 1a and separating filler material 34. This circuit being connected electrically only to the two 1b magnet force units. The rigid tubes 20 20 21 21 and flexible elastic tubes 20c 20c and 21c 21c have not been completely identified throughout for the sake of clarity. A moveable end cap 26 closes one end of the motion producing device while a relatively fixed electrical connection end cap 27 closes the other end. A protective and guiding sheath 25 encircles the device.

Figure 5:
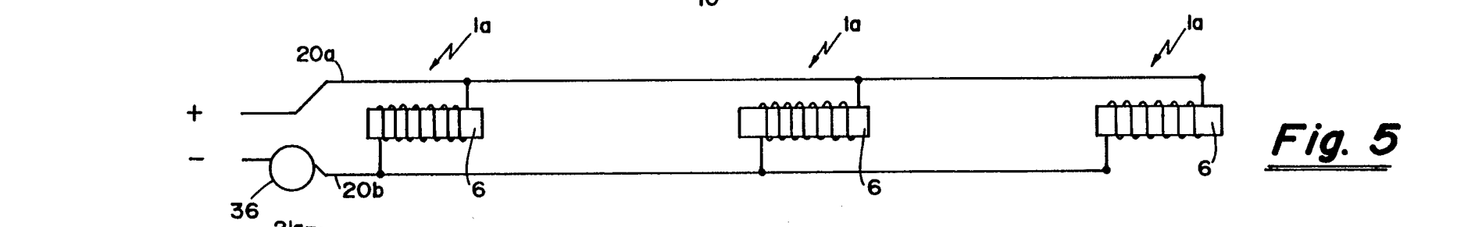
FIG. 5 is a schematic of single fixed polarity variable electro magnets in parallel as could be used in FIG. 4.

Looking now at FIG. 5 there is shown only a simplified schematic drawing of the second circuit showing only single electromagnets 6 for the fixed polarity magnetic force units 1a with a rheostat 36 for current control.

Figure 6:
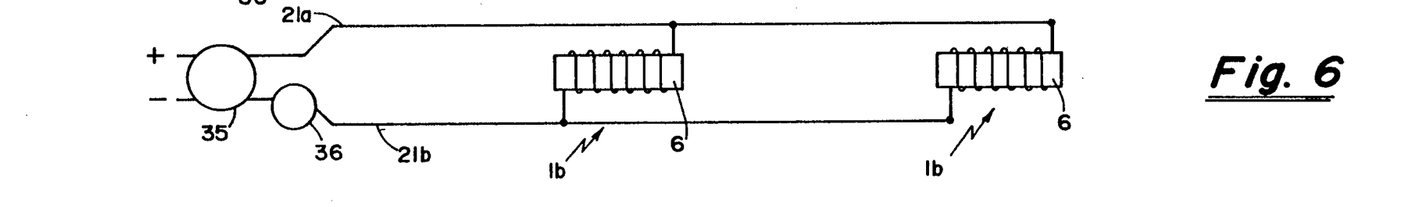
FIG. 6 is a schematic of single reversible polarity variable electromagnets in parallel as could be used in FIG. 4.

Looking now at FIG. 6 there is shown only a simplified schematic drawing of the first circuit showing only single electromagnets 6 for the reversible polarity magnetic force units 1b with a rheostat 36 for current control and a polarity reverser 35 for reversing the polarity of the circuit.

Figure 7:
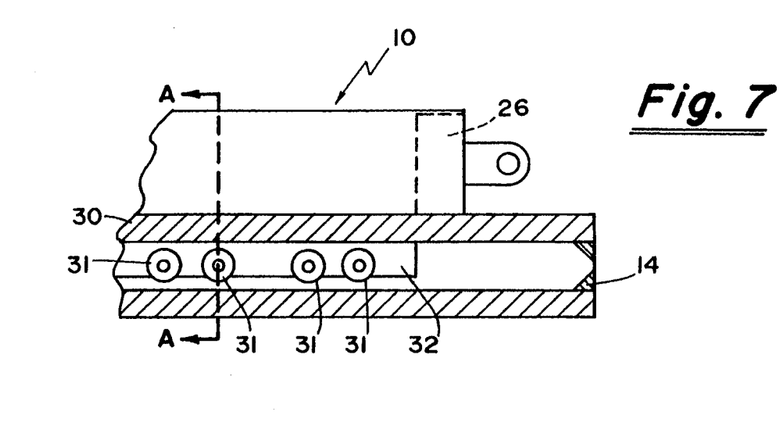
FIG. 7 is a vertical side section B—B of FIG. 8, showing a truck guide assembly.
Figure 8:
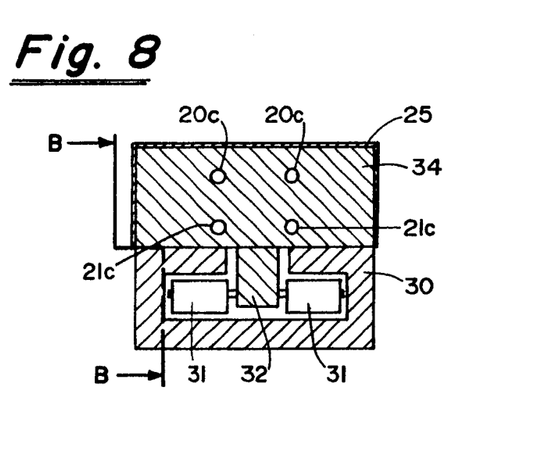
FIG. 8 is a vertical end view of section A—A of FIG. 7, of a motion producing device with truck guide assembly.

Referring now to FIG. 7 a partially sectioned view B—B of FIG. 8 shows a truck type guiding system included with the motion producing device 10. The motion producing device 10 with coupler end cap 26 includes a guide truck support 32 attached therebelow. Guide truck rollers 31 are rotatably attached to the guide truck support 32. Guiding the guide truck rollers 31 is a channel guide rail 30. To prevent over extension of the motion producing device 10 a guide rail stop 14 has been mounted at the end of the channel guide rail 30.

Looking now at FIG. 8, a section A—A of FIG. 7, there is shown an end section of the elastic nonconductor filler material 34, a guide truck support 32 depending therefrom and rotatably supporting guide truck rollers 31. The rollers 31 are guided by a channel guide rail 30. The flexible elastic tubes 20c 20c and 21c 21c are embedded in the elastic nonconductive filler material 34.

Figure 9:
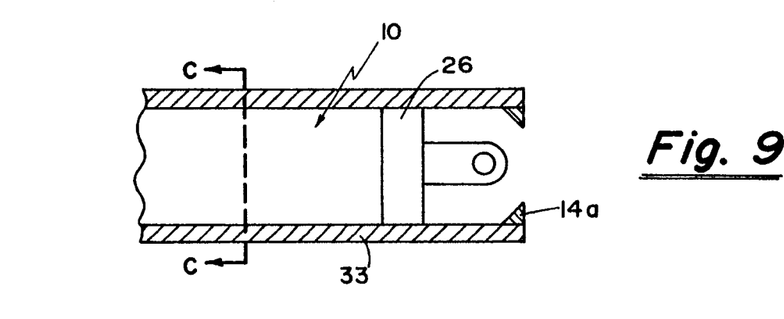
FIG. 9 is a vertical side section D—D of FIG. 10, of a motion producing device using an outer guide control tube.
Figure 10:
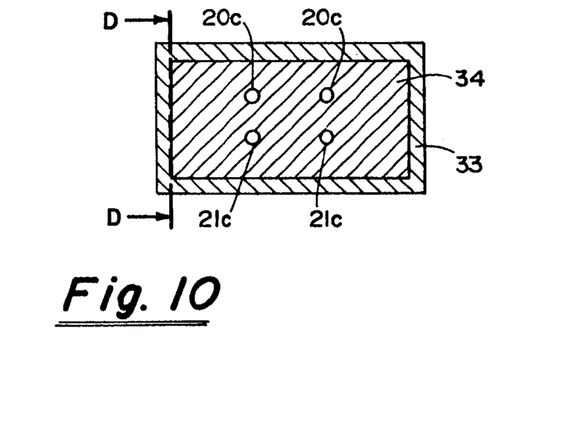
FIG. 10 is a vertical end view section C—C of FIG. 9 of a motion producing device using an outer guide control tube.

The FIG. 9 illustrates a simplified form of guide means as viewed from the cutting plane D—D of FIG. 10. A motion producing device 10 is varied by being surrounded by an outer guide control tube 33 with guide tube stop 14a. The motion producing device 10 again carrying its coupler end cap 26.

The FIG. 10 illustrates an end view of the motion producing device 10 with outer guide control tube 33 taken at the cutting plane C—C of FIG. 9 which is through elastic nonconductive filler material 34. The flexible elastic tubes 21c 21c of the first circuit and flexible elastic tubes 20c 20c of the second circuit are embedded in the filler material 34.

Figure 11:
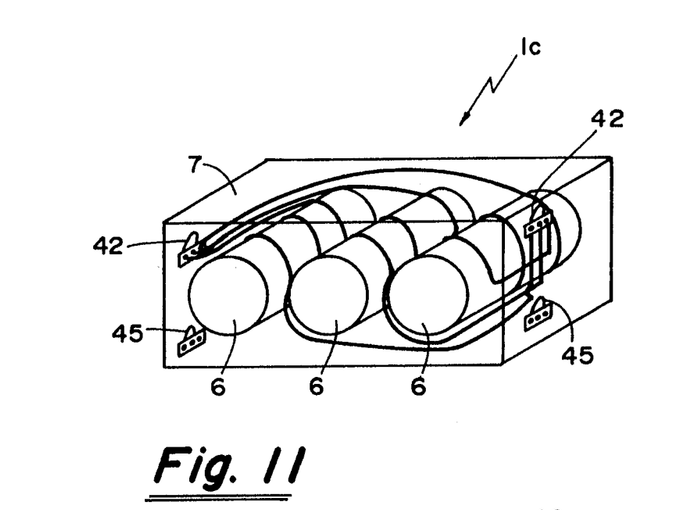
FIG. 11 is a perspective view of a second embodiment of a magnetic force unit.
Figure 12:
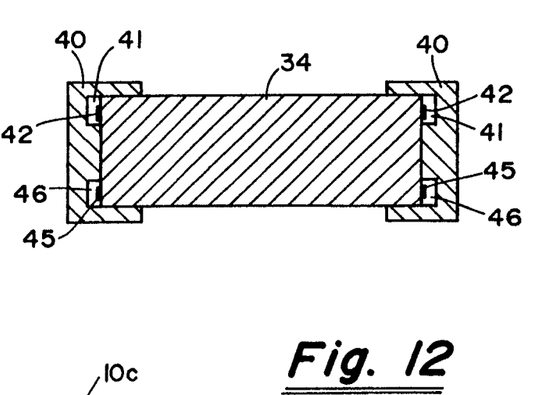
FIG. 12 is an enlarged sectional end view A—A of FIG. 13.
Figure 13:
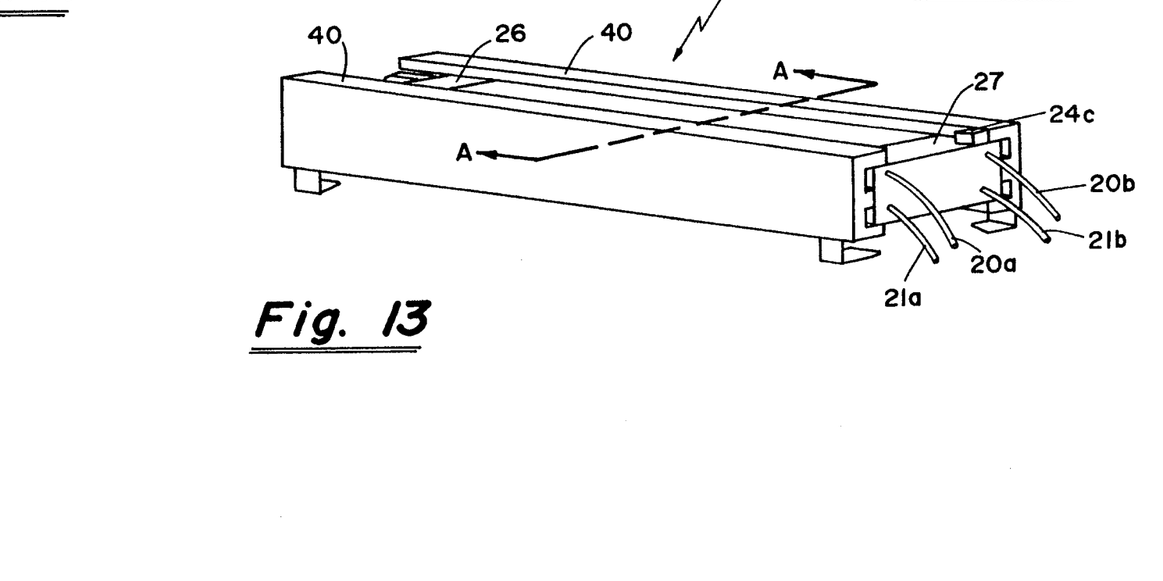
FIG. 13 is a perspective view of the second embodiment using side guide rails and slideable contacts.

Now looking at a second embodiment illustrated in FIGS. 11, 12 and 13. A basic magnetic force unit 1c is shown in perspective in FIG. 11. There is again shown 3 electromagnets 6 side by side and immersed in a rigid nonconductive material 7. Embedded in the sides of the rigid nonconductive material 7 are terminals 42 42 having a slideable, moveable or flexible contact means. The electromagnets 6 are here connected to the top terminal 42 42 and are being described as being part of a first circuit carrying current to the fixed polarity electromagnets fed by leads 20a and 20b.

Referring now to FIG. 12 there is shown an end view cross section taken at the cutting plane A—A in FIG. 13. There are two guide rails 40 40, one on each side of the slideable contact motion producing device 10c. The cutting plane has been taken where one elastic nonconductive filler material 34 separates adjacent magnetic force units. Embedded in the rigid nonconductive material 7 are the visible protruding terminals 42 42, and protruding terminals 45 45 which have either moveable or flexible contacts to contact strip conductors 41 41 and 46 46 carried by the guide rails 40 40.

Referring now to FIG. 13 there is illustrated a slideable contact motion producing device 10c made up of a series of slideable contact magnetic force units 1c each separated from the other by elastic nonconductive filler material 34. A first end is capped by an electrical connection end cap 27 carrying leads 20a 20b 21a 21b and fixed to a guide rail 40 by movement retainer 24c.

A third obvious embodiment (not illustrated) is a combination of a series of the magnetic force units of FIG. 1 with the separating elastic nonconductive filler material 34 therebetween and the electromagnets being energized by a strip conductor in the form of guide rods passing through the metallic tubes 20 20 21 21. No flexible electrolyte carrying elastic tubes in the filler material 34 would be necessary.

Figure 14:
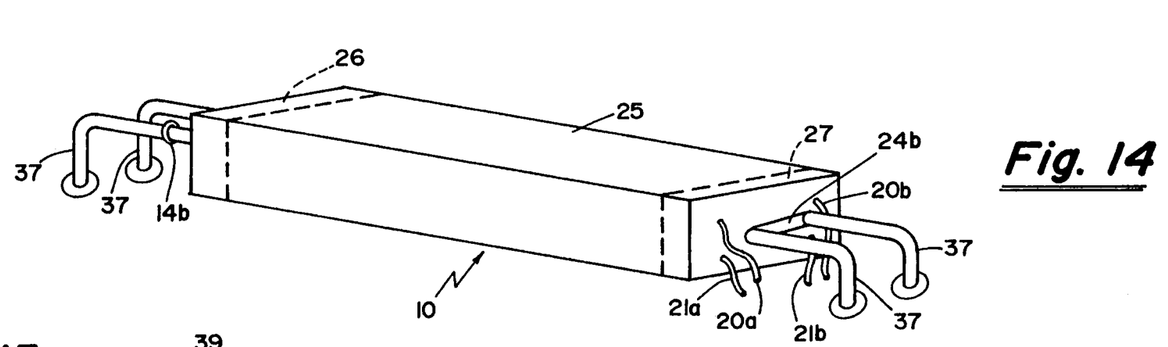
FIG. 14 is a perspective view showing guide rods passing longitudinally of the first embodiment motion producing device.

The illustration in FIG. 14 teaches the basic motion producing device 10 with bent guide rods 37 slideably passing longitudinally through the rigid nonconductive material 7 the separating elastic nonconductive filler material 34 and the coupler end cap 26 and the electrical connection end cap 27. A reaction or movement retainer 24b fastens the motion producing device 10 to the guide rods 37 while a guide rod stop 14b limits the movement of the device longitudinally.

Figure 15:
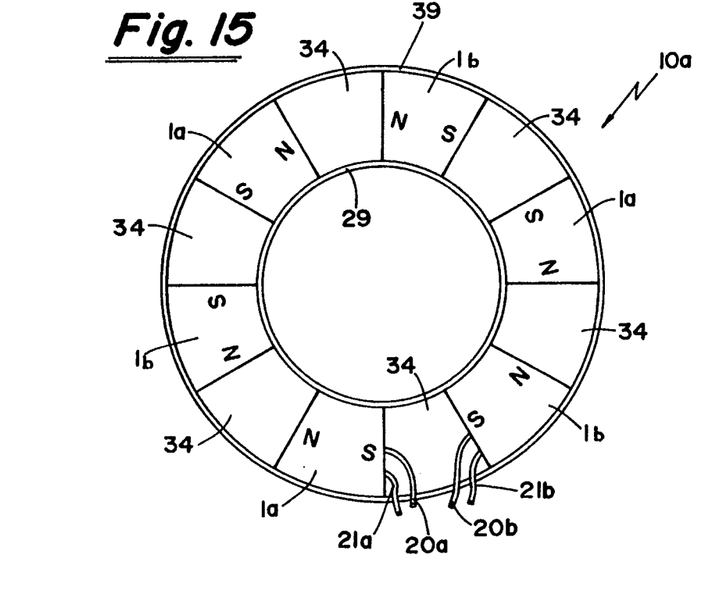
FIG. 15 is a circular arrangement of the motion producing device in the expanded form.
Figure 16:
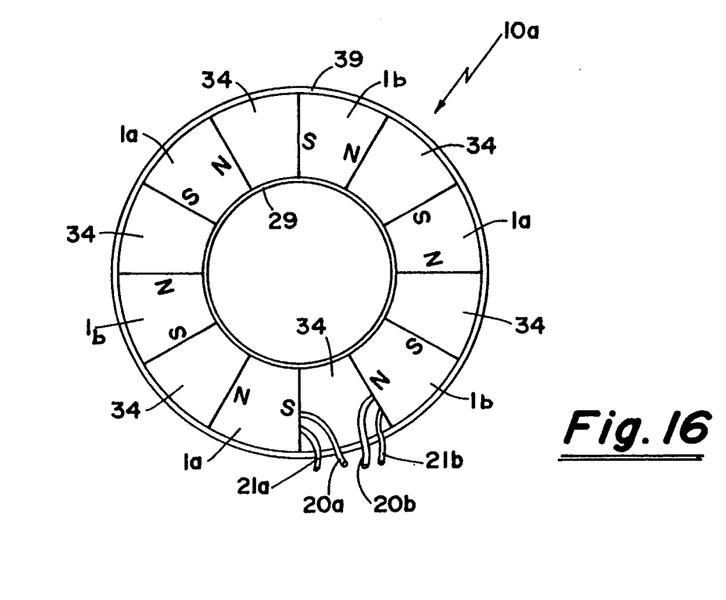
FIG. 16 is a circular arrangement of the motion producing device in the contracted form.

The form variations shown in FIG. 15 and FIG. 16 also teach the basic motion producing device 10 designated 10a, in a circular form requiring no coupler end cap 26 or electrical connection end cap 27. The electrical leads 20a 20b 21a 21b enter at one of the elastic nonconductive filler material units 34. An elastic outer wall 39 and an elastic inner wall 29 protect and guide the movement of the device 10 as it expands and contracts. The circular contraction and expansion embodiment is unlimited in use but is particularly useful in pumping. FIG. 15 is expanded, FIG. 16 is contracted.

Figure 17:
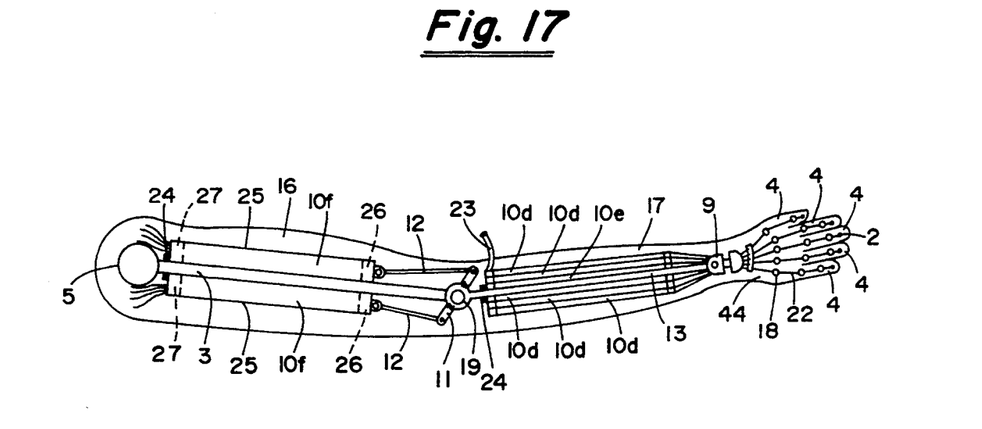
FIG. 17 illustrates the use of multimotion producing devices in the operation of an artificial arm and hand in the extended position.
Figure 18:
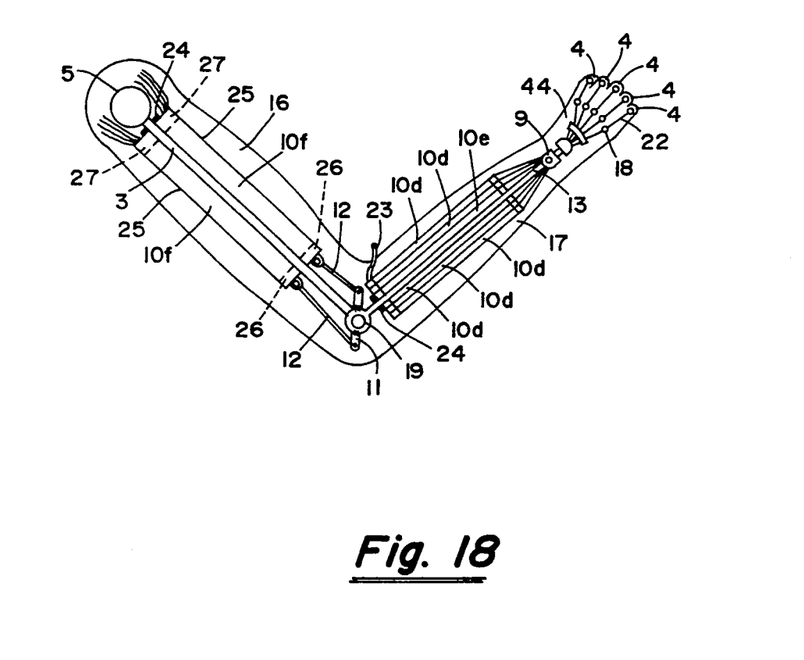
FIG. 18 illustrates the use of multimotion producing devices in the operation of an artificial arm and hand in the contracted position.

Referring now to FIG. 17 and FIG. 18 there is shown an artificial arm firstly in the extended position and secondly in the contracted or pivoted position. In FIG. 17 we have an arm that could be affixed to an object at the ball and socket joint 5 for pivotal movement. The arm is shown as basically including a primary body 16, a secondary body 17 and a multidigit appendage 44, all pivotally linked. The primary body 16 has a primary frame 3 attached to the ball and socket joint 5 and extends longitudinally therefrom coaxially with the primary body 16. The primary frame 3 may be constructed of various types of material in various cross sectional shapes. Attached to the primary frame 3 are at least two forearm moving motion producing devices 10f which can be of the form 10 or 10c. The motion producing devices 10f are attached longitudinally to the primary frame 3 by a movement retainer 24. The motion producing devices 10f must be laterally restrained by slideable fixing means to the primary frame 3 or by the elastic flesh like material forming the primary body 16. Attached to the coupler end caps 26 are connecting links or rods 12 which are pivotally connected to a double lever 11 made integral with an eye which is pivotal about a pivot pin 19 fixed to the extended end of primary frame 3. Integral with the eye is a secondary frame 13 which also can be made in various shapes and of various materials. The secondary frame 13 has mounted thereon five relatively small motion producing devices 10d for moving the five fingers 4 and one relatively small motion producing device 10e for moving wrist swivel hinge joint 9. The motion producing devices 10d and 10e can be of the form 10 or 10c or a combination thereof. A movement or reaction retainer 24 fixes the motion producing devices 10d and 10e to the secondary frame 13. The motion producing devices 10d and 10e must also be laterally restrained by slideable fixing means to the secondary frame 13 or by the elastic flesh like material forming the secondary body 17. Controls for the fingers or digits 4 are fed in at tendon controller 23. Finger tendons 22 in the multidigit appendage 44 are generally in the form of "Bowden" (or the like) cables and are attached at 2 to the fingers or digits 4. Application of the motion producing devices 10d cause the fingers or digits 4 to curl in a grasping motion or extend in a releasing motion.

FIG. 18 shows the same artificial arm with movement of the double lever 11 when the polarity of the reversible polarity magnets has been reversed relative to the operation in FIG. 17. In FIG. 17 the top link 12 is extended and the bottom link 12 has been retracted. In FIG. 18 the top link 12 has been retracted and the bottom link 12 extended thereby pivoting the forearm or secondary body 17. In FIG. 18 the finger or digit motion producing devices 10d have had the reversible polarity magnets reversed and the fingers or digits are now in a grasping mode.

For clarification purposes it should be noted that the first basic embodiment description and related claims have recited the reversible polarity magnets as being in a first circuit and the fixed polarity magnets as being in a second circuit while in the second basic embodiment and related claims the fixed polarity magnets are recited as being in a first circuit and the reversible polarity magnets as being in a second circuit. The two basic embodiments are in fact functionally identical regardless of the nomenclature of the circuitry.

Various modifications such as size, shape and arrangement of components may be made without departing from the spirit and scope of this invention. The above disclosure shall be interpreted as illustrative only and limited only by the scope of the invention as defined in the following claims.

What I claim is:

1. A motion producing device utilizing magnetic lines of force comprising in combination, a series of magnetically linked magnetic force units, said series formed by a magnetic force unit including at least one fixed polarity magnet alternating with a next adjacent magnetic force unit including at least one reversible polarity magnet, each said magnetic force unit further including rigid electrically nonconductive material surrounding each said fixed polarity magnet and said reversible polarity magnet, first rigid electricity carrying means embedded in said rigid electrically nonconductive material of each said magnetic force units, an elastic electrically nonconductive filler separating each of said magnetic force units, first elastic electricity carrying means embedded in said elastic electrically nonconductive filler and joined in series with said first rigid electricity carrying means of each said adjacent magnetic force units forming a first circuit, an elastic electrically nonconductive outer sheath supporting and protecting said series, said at least one reversible polarity magnet being an electromagnet, an electrical power source connected to said at least one electromagnet through said first circuit and a polarity reversing means in said first circuit, whereby reversing the polarity of said first circuit reverses the polarity of said at least one electromagnet changing the direction of said magnetic lines of force thereby providing an expanding or contracting motion of said motion producing device, like adjacent poles causing expansion and unlike adjacent poles causing contraction.

2. A motion producing device as claimed in claim 1 further including a coupler end cap at a first end of said series of magnetic force units and an electrical connector cap at a second end of said series of magnetic force units supporting a portion of said first circuit and wherein said at least one fixed polarity magnet is a permanent magnet.

3. A motion producing device as claimed in claim 1 wherein said series of magnetic force units includes more than one magnetic force unit having a fixed polarity magnet and more than one magnetic force unit having a reversible polarity magnet, 4. A motion producing device as claimed in claim 3 wherein each magnetic force unit having at least one reversible polarity magnet contains two or more reversible polarity magnets that are all electromagnets and are connected in parallel with said power source on said first circuit.

5. A motion producing device as claimed in claim 4 wherein each magnetic force unit having at least one fixed polarity magnet contains two or more fixed polarity magnets that are all electromagnets and are connected in parallel with said power source on a second circuit formed of a joined series of second rigid electrical carrying means and second elastic electrical carrying means.

6. A motion producing device as claimed in claim 5 further including a rheostat in said first circuit and said second circuit to increase or decrease the strength of said electromagnets in each of said circuits separately.

7. A motion producing device as claimed in claim 6 wherein said series of magnetic force units are linearly aligned.

8. A motion producing device as-claimed in claim 6 wherein said series of magnetic force units are circularly formed.

9. A motion producing device as claimed in claim 7 further including means for guiding movement of said series of magnetic force units.

10. A motion producing device as claimed in claim 9 wherein said guide means includes guide trucks rolling in a channel guide rail with guide truck stop, an extension of said magnetic force units are fastened to one or more of said guide trucks.

11. A motion producing device as claimed in claim 9 wherein said guide means is formed of a rigid outer tubing encompassing said series of magnetic force units permitting only longitudinal movement thereof and a tube stop formed at an end of said rigid outer tubing to limit travel of said series of magnetic force units.

12. A motion producing device as claimed in claim 9 wherein said guide means includes guide rods with limiting stop, slideably penetrating longitudinally said series of magnetic force units.

13. A motion producing device utilizing magnetic lines of force comprising in combination: a power source, a longitudinal series of magnetically linked magnetic force units, said series formed by a magnetic force unit including at least one fixed polarity magnet alternating with a next adjacent magnetic force unit including at least one reversible polarity magnet, each said magnetic force units further including rigid nonelectrically conductive material surrounding each said fixed polarity magnet and said reversible polarity magnet, a plurality of first electricity carrying means connected to said fixed polarity magnets and embedded in said rigid nonelectrically conductive material of each related said magnetic force units, an elastic nonelectrically conductive filler separating all adjacent magnetic force units, longitudinal guide means for guiding said series of force units in motion, a plurality of second electricity carrying means carried by said longitudinal guide means and slideably contacting said plurality of first electricity carrying means to form with said power source a first circuit for carrying power to said fixed polarity magnets, a plurality of third electricity carrying means connected to said reversible polarity magnets and embedded in said rigid nonelectrically conductive material of each related said magnetic force units, a plurality of fourth electricity carrying means carried by said longitudinal guide means and slideably contacting said plurality of third electricity carrying means to form with said power source a second circuit for carrying current to said reversible polarity magnets, said second circuit including a polarity reverser, whereby reversing the polarity of said second circuit reverses the polarity of said reversible polarity magnets thereby causing an expansion or contraction of the device due to the magnetic laws of repulsion and attraction applied to the magnets.

14. A motion producing device as claimed in claim 13 wherein said longitudinal guide means externally engages opposite sides of said longitudinal series of force units and wherein said plurality of first electricity carrying means and said plurality of third electricity carrying means includes moveable contacts protruding from said rigid nonelectrically conductive material.

15. A motion producing device as claimed in claim 13 wherein said plurality of first electricity carrying means, and said plurality of third electricity carrying means are metallic tubes embedded in said rigid nonelectrically conductive material and, wherein said longitudinal guide means are guide rods slideably supported by said metallic tubes.

16. A motion producing device utilizing magnetic lines of force comprising in combination, a series of alternately spaced fixed and polarity reversible magnets, electrically insulating material surrounding each magnet of said series of magnets, elastic electrically insulating material mounted between each adjacent fixed and polarity reversible magnets, a power source, current conducting means for carrying current to at least said polarity reversible magnets from said power source, a polarity reversing means in said current conducting means that reverses the polarity of said current conducting means to said at least polarity reversible magnets, and guide means to control expansion or contraction movement of said series as said power source is applied.

* * * * *